(12) United States Patent
Richart

(10) Patent No.: US 10,752,405 B2
(45) Date of Patent: Aug. 25, 2020

(54) DEVICE FOR PACKAGING AN OBJECT AND CORRESPONDING METHOD OF EXTRACTION

(71) Applicant: SELENIUM MEDICAL, La Rochelle (FR)

(72) Inventor: Olivier Richart, Lagord (FR)

(73) Assignee: SELENIUM MEDICAL, La Rochelle (FR)

( * ) Notice: Subject to any disclaimer, the term of this patent is extended or adjusted under 35 U.S.C. 154(b) by 0 days.

(21) Appl. No.: 16/338,921

(22) PCT Filed: Oct. 5, 2017

(86) PCT No.: PCT/FR2017/052734
§ 371 (c)(1),
(2) Date: Apr. 2, 2019

(87) PCT Pub. No.: WO2018/065733
PCT Pub. Date: Apr. 12, 2018

(65) Prior Publication Data
US 2020/0010244 A1 Jan. 9, 2020

(30) Foreign Application Priority Data
Oct. 6, 2016 (FR) ..................................... 16 59654

(51) Int. Cl.
*B65D 25/10* (2006.01)
*B65D 25/28* (2006.01)
(Continued)

(52) U.S. Cl.
CPC ........ *B65D 25/2814* (2013.01); *A61F 2/0095* (2013.01); *B65D 25/102* (2013.01); *B65D 83/0005* (2013.01)

(58) Field of Classification Search
CPC .............. B65D 25/102; B65D 25/2814; B65D 83/0005; A61F 2/0095
(Continued)

(56) References Cited

U.S. PATENT DOCUMENTS 4,856,648 A * 8/1989 Krueger ............... A61C 8/0087
206/63.5
5,538,428 A * 7/1996 Staubli ................. A61C 8/0087
206/63.5
(Continued)

OTHER PUBLICATIONS

International Search Report dated Apr. 28, 2017.

*Primary Examiner* — Luan K Bui
(74) *Attorney, Agent, or Firm* — Ipsilon USA, LLP

(57) ABSTRACT

The invention provides a packaging device for packaging an object, the device comprising a tube (1) that is open (10) at one end and a stopper (2). The packaging device comprises a strip (3) of length greater than the length of the tube (1). Said strip (3) has a coupling system (4) enabling an object (5) to be coupled to said strip (3). Together with the tube (1), the strip (3) is configured to occupy a first position in which the strip (3) is held compressed inside the tube (1) by the stopper (2), said strip (3) presenting a first end (310) in bearing contact with the end wall of the tube (1) opposite from the said opening (10), and a second position in which, after the stopper (2) has been removed, the strip (3) presents a second end (320), opposite from said first end, that projects out through the opening (10) of the tube (1). The invention also provides a corresponding method of extraction.

10 Claims, 6 Drawing Sheets

(51) Int. Cl.
*A61F 2/00* (2006.01)
*B65D 83/00* (2006.01)

(58) Field of Classification Search
USPC .............. 206/63.3, 63.5, 363–370, 438
See application file for complete search history.

(56) References Cited

U.S. PATENT DOCUMENTS

| | | | | |
|---|---|---|---|---|
| 5,622,500 | A * | 4/1997 | Niznick | A61C 8/0048 |
| | | | | 206/63.5 |
| 5,636,991 | A * | 6/1997 | Mays | A61C 19/02 |
| | | | | 206/368 |
| 5,755,575 | A * | 5/1998 | Biggs | A61C 8/0087 |
| | | | | 206/63.5 |
| 5,967,305 | A * | 10/1999 | Blonder | A61C 8/0087 |
| | | | | 206/486 |
| 6,217,332 | B1 * | 4/2001 | Kumar | A61C 8/0087 |
| | | | | 206/368 |
| 6,913,465 | B2 * | 7/2005 | Howlett | A61C 8/0087 |
| | | | | 206/63.5 |
| 2003/0214139 | A1 | 11/2003 | Nigam | |
| 2009/0057167 | A1 * | 3/2009 | Rathert | A61F 2/1691 |
| | | | | 206/205 |
| 2014/0042050 | A1 * | 2/2014 | Richart | A61B 17/865 |
| | | | | 206/438 |
| 2017/0042628 | A1 | 2/2017 | Richart | |

* cited by examiner

DEVICE FOR PACKAGING AN OBJECT AND CORRESPONDING METHOD OF EXTRACTION

RELATED APPLICATION

This application is a National Phase of PCT/FR2017/052734, filed on Oct. 5, 2017, which claims the benefit of priority from French Patent Application Nos. 16 59654, filed on Oct. 6, 2016, the entirety of which are incorporated by reference.

FIELD OF THE INVENTION

The present invention relates in general manner to packaging an object, and in particular to packaging a medical implant.

PRIOR ART

The state of the art, and in particular Document FR 2 959 216 A1, discloses packaging a medical implant by positioning it inside a tube that is closed by a stopper. In particular, it is known that the stopper may be provided with a system for attaching the implant. The operator can thus remove the stopper so as to extract the implant from the tube. Thereafter, the operator deactivates the implant attachment system in order to be able to grip the implant and use it.

Nevertheless, it is found that such attachment systems known in the state of the art are expensive to fabricate and/or not very practical for handling by the operator. In addition, such attachment systems known in the state of the art can mask a portion of the implant, which can be a source of error or of complication for the operator seeking to be able quickly to identify visually the implant contained in the tube.

An object of the present invention is to provide a novel packaging method and device enabling some or all of the above-described problems to be mitigated.

SUMMARY OF THE INVENTION

To this end, the invention provides a packaging device for packaging an object, the device comprising:
- a tube that is open at one end;
- a stopper enabling said opening of the tube to be closed; and
- an object, such as a medical implant;

the packaging device being characterized in that it comprises a flexible elongate element referred to as a "strip";

said strip being of length greater than the length of the tube, said strip having a coupling system enabling said object to be coupled to said strip;

together with the tube, the strip being configured to occupy:
- a first position in which the strip is held compressed inside the tube by the stopper, said strip presenting a first end in bearing contact with the end wall of the tube opposite from the said opening; and
- a second position in which, after the stopper has been removed, the strip presents a second end, opposite from said first end, that projects out through the opening of the tube.

The strip is thus long enough to be capable of presenting an end that projects from the tube when the stopper has been removed, thereby making it easier to grasp, and also to bear via its other end against the end wall of the tube, which end wall thereby constitutes a bearing point for the end of the strip and avoids the strip becoming jammed in the tube via the object with which it is coupled, as can happen if the length of the strip is not sufficient to engage the end wall of the tube.

The end of the strip bearing against the end wall of the tube enables the object that is coupled to the strip to be maintained at a certain distance along the tube. The compression applied by the stopper on the strip serves to stress the strip and thus limit or even prevent any movement of the strip and thus of the object relative to the tube, while benefiting from the return force that tends to return the strip to its relaxed position when the stopper is removed and that opposes the object becoming jammed in the tube.

According to an advantageous characteristic of the invention, the tube is translucent or transparent.

By combining the use of a strip to which the object is coupled with a tube that is transparent or translucent, it is possible for the user to see the object easily, since it is held at a given distance along the tube, e.g. halfway along the tube. The user can thus quickly and reliably identify the object contained in the tube even before the tube is opened.

According to an advantageous characteristic of the invention, the strip is translucent or transparent.

According to an advantageous characteristic of the invention, the coupling system comprises an element suitable for snap-fastening with an orifice formed in the object.

According to an advantageous characteristic of the invention, said coupling system comprises an enlarged portion of the strip, preferably situated in the middle of the strip, that forms a base, two lugs being formed by being cut out in said base, said lugs being suitable for being stood up relative to said base, so as to be brought one against the other in order to be passed through an orifice formed in the object, said lugs being suitable for returning to a mutually spaced-apart position after passing through the orifice in the object, in which position the possibility of removing the object is limited.

According to an advantageous characteristic of the invention, said coupling system comprises two spaced-apart parallel slots formed through the strip in order to form a loop in which an object, such as a screw, can be inserted.

According to an advantageous characteristic of the invention, the strip is in the form of a rack presenting a series of detents and the coupling system comprises two sliders that can be moved towards each other along the rack in order to clamp onto the object, the detents being configured to prevent said sliders from moving away from each other.

According to an advantageous characteristic of the invention, the tube and the strip are shaped in such a manner as to limit or prevent the strip from turning relative to the tube.

According to an advantageous characteristic of the invention, said device includes said object, said object being coupled to the strip and being contained in the tube.

According to an advantageous characteristic of the invention, a first orifice and a second orifice are formed in the object in order to pass one end portion of the strip through the first through orifice and pass an opposite end portion of the strip through the second through orifice, in such a manner that the coupling system of the strip extends on one side of the object and the end portions extend mainly on the other side.

According to an advantageous characteristic of the invention, the coupling system comprises a portion of the strip, referred to as a "stop portion", that is spaced apart from the ends of the strip, and that is of width greater than the width of the end portions of the strip and greater than the width of the first and second through orifices formed in the object.

The invention also provides a method of extracting the object from a packaging device as described above, said method comprising the following steps:

removing the stopper in order to open the tube;

the operator gripping in one hand the end portion of the strip that projects through the opening of the tube;

gripping in another hand the object coupled to the strip; and decoupling the object from the strip.

BRIEF DESCRIPTION OF THE DRAWINGS

Other characteristics and advantages of the invention appear further from the following description, which is purely illustrative and non-limiting and should be read with reference to the accompanying drawings, in which.

DETAILED DESCRIPTION

Figure 1:
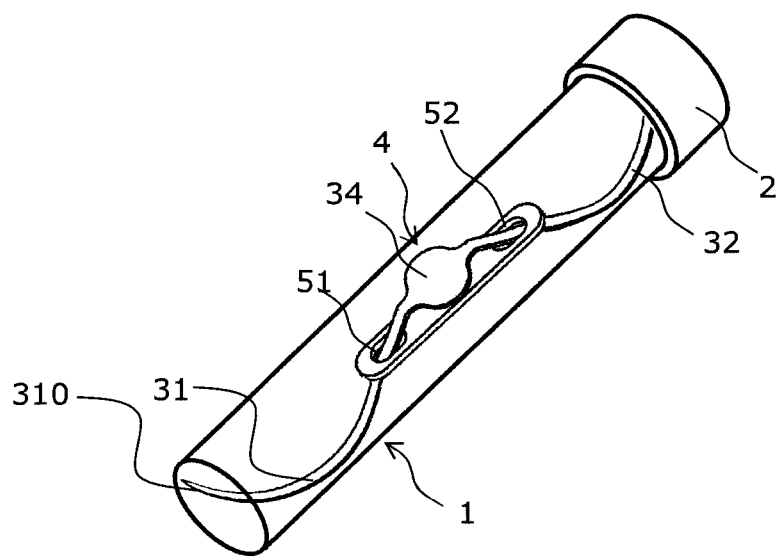
FIG. 1 is a view of a tube closed by a stopper, said tube containing an implant coupled to a flexible strip, in accordance with a first embodiment of the invention.

The concept of the invention is described more completely below with reference to the accompanying drawings, which show embodiments of the concept of the invention. Similar numbers refer to similar elements in all of the drawings. Nevertheless, the concept of the invention may be implemented in numerous different forms and should not be interpreted as being limited to the embodiments described herein. Instead of that, these embodiments are proposed so that the description is complete and communicates the extent of the concept of the invention to persons skilled in the art. Consequently, the extent of the invention is defined by the accompanying claims.

Throughout the description, any reference to "an embodiment" means that a particular function, structure, or characteristic described with reference to one embodiment is included in at least one embodiment in the present invention. Thus, the appearance of the term "in an embodiment" at various locations throughout the description does not necessarily refer to the same embodiment. In addition, the particular functions, structures, or characteristics may be combined in any appropriate manner in one or more embodiments.

With reference to the figures, and as summarized above, the invention relates to a device for packaging an object. In the example shown in the figures, said object is a medical implant.

Said device comprises a tube 1 that is open at one end. A stopper 2 serves to close the opening 10 of the tube. The tube contains an object 5, such as a medical implant.

The packaging device also includes a flexible elongate element, referred to as a strip 3.

Said strip 3 includes a coupling system 4 enabling said object 5 to be coupled to said strip 3. As described in detail below, the object can be uncoupled from the strip.

The strip is flexible about an axis parallel to the mean plane of the strip and orthogonal to the longitudinal axis of the strip.

The strip 3 is flexible, so that when it is not under stress, the strip presents a given shape that is substantially straight, and when the strip is spread in compression, the strip is compressed like a spring blade, but is urged back into its initial shape when the stress to which it was subjected is removed.

Like a bendable blade, the strip 3 may be compressed, being held under stress by the stopper, and it can return to its substantially straight initial shape when the stopper is removed, i.e. when the strip is no longer stressed.

Together with the tube 1, the strip 3 is configured to occupy a first position in which the strip 3 is held compressed inside the tube 1 by the stopper 2. In this first configuration, the strip 3 presents a first end 310 in bearing against the end wall of the tube 1 remote from said opening 10. Together with the tube 1, the strip 3 is also configured to occupy a second position in which, once the stopper 2 has been removed, the strip 3 is no longer stressed by the stopper and presents a second end 320, remote from said first end 310, that projects out through the opening 10 of the tube 1.

In particular, said strip 3 is of length greater than the length of the tube 1 so that when the stopper is removed and the strip is therefore not stressed, said strip presents an end that projects out through the opening 10 of the tube 1.

Advantageously, the tube 1 is translucent or transparent. Preferably, the strip 3 is also translucent or transparent. This enables the user to identify the object contained in the tube quickly and easily. In each of the embodiments shown in FIGS. 1 to 9, a first orifice 51 and a second orifice 52 are formed in the object 5 to allow an end portion 31 of the strip 3 to pass through the first through orifice 51 and to allow an opposite end portion 32 of the strip 3 to pass through the second through orifice 52, so that the coupling system 4 of the strip 3 projects from one side of the object 5, i.e. from one side of the orifices, while the end portions 31 and 32 extend mainly on the other side.

The first and second end portions 31 and 32, referred to respectively as first and second strands, may be defined as the portion of the strip that extends between the first or second end 310, 320 of the strip and the object coupling system 4. The object coupling system 4 may be made of various materials, as described in detail below.

Figure 2:
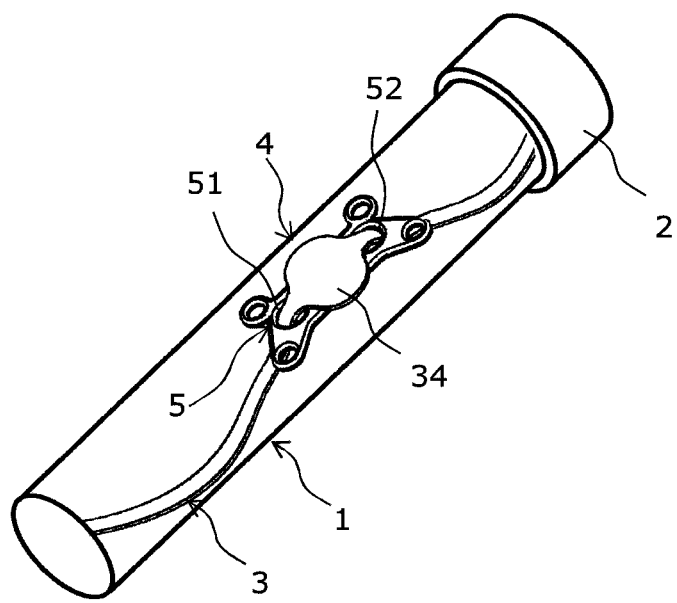
FIG. 2 is a view of a tube closed by a stopper, said tube containing an implant coupled to a flexible strip, in accordance with a second embodiment of the invention.

In the embodiments shown in FIGS. 1 and 2, the coupling system 4 comprises a portion 34 of the strip 3 that is referred to as a "stop portion", which portion is remote from the ends 310 and 320 of the strip, and is of a width that is greater than the width of the end portions 31 and 32 of the strip 3. The width of the stop portion is also greater than the width of the first and second through orifices 51 and 52 formed in the object 5.

As shown in the embodiments of FIGS. 1 and 2, said stop portion 34 forms a stop zone for stopping the object 5 along the strip 3. Specifically, the width of the stop portion 34 is greater than the corresponding width, i.e. the width taken in the same direction, of the through orifices 51 and 52 formed in the object, thereby serving to form an abutment for stopping the strip 3 from sliding along its longitudinal axis relative to the object 5 in either direction.

In the example shown in FIG. 1, the object is an example of a surgical plate for bone fastening (arthrodesis, metatarsalphalangeal compressions, . . . ) in the form of an oblong part having the two through orifices 51, 52 formed therein. In this embodiment, said through orifices 51, 52 are oblong and are situated in the proximity of opposite ends of said part.

In the example shown in FIG. 2, the object is an example surgical plate for bone fastening that is in the form of a part having four lugs arranged at four corners of the part. Said part also presents the two through orifices 51 and 52 that are situated in the proximity of the opposite ends of said part.

Figure 3:
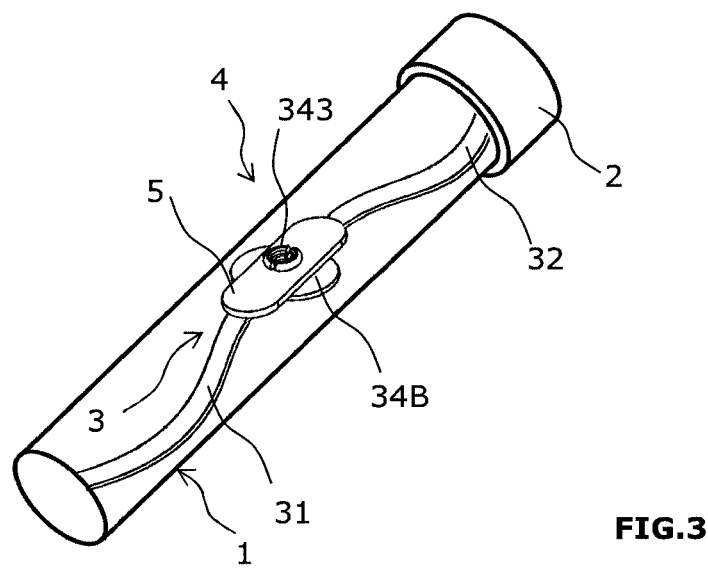
FIG. 3 is a view of a tube closed by a stopper, said tube containing an implant coupled to a flexible strip, in accordance with a third embodiment of the invention.

In the embodiment shown in FIG. 3, in which the object 5 is an example surgical plate for bone fastening, the coupling system 4 comprises a snap-fastening element 343 that can be snap-fastened in an orifice formed in the object 5. In other words, said element 343 is elastically deformable and is configured to be capable of deforming by retracting on passing through said orifice made in the object 5 and to be capable of returning to its previous shape after it has passed through the orifice.

Advantageously, said coupling system also includes an enlarged portion 34B of the strip that is preferably situated in the middle of the strip, and that forms a base on which said snap-fastening element is situated. As shown in FIG. 3, said snap-fastening element 343 is in the form of a mushroom having a split cap to enable it to deform elastically in order to pass through the orifice in the object 5.

Figure 4:
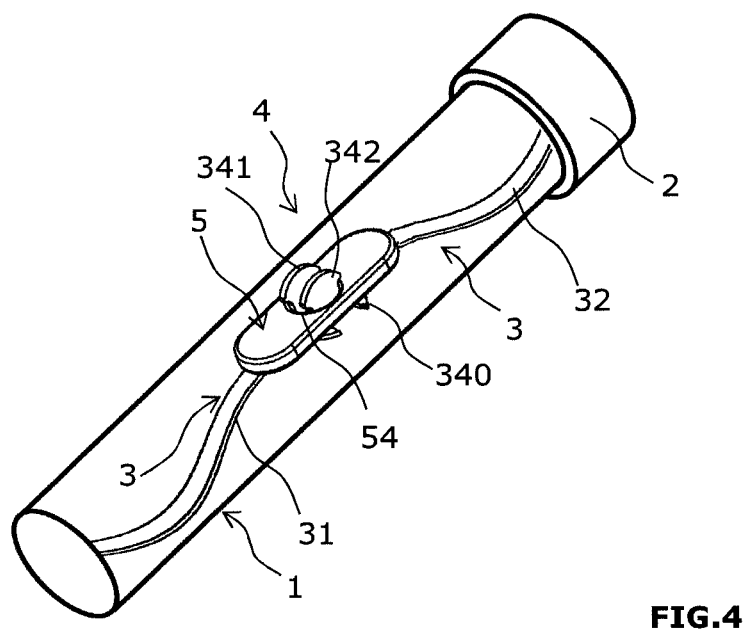
FIG. 4 is a view of a tube closed by a stopper, said tube containing an implant coupled to a flexible strip, in accordance with a fourth embodiment of the invention.

In the embodiment shown in FIG. 4, in which the object is an example surgical plate for bone fastening, said coupling system 4 comprises an enlarged portion of the strip that is preferably situated in the middle of the strip 3, and that forms a base 340. Two lugs 341 and 342 are cut out in said base 340. Said lugs 341 and 342 are suitable for being stood up relative to said base 340, so as to be brought one against the other, and then for being passed through an orifice 54 formed in the object. Said lugs 341 and 342 are then suitable for returning to a position in which they are spaced apart from each other after passing through the orifice 54 in the object, in which position the possibility for removing the object 5 is limited.

As shown in FIG. 4, said lugs may present notches forming teeth that oppose removal of the lugs 341 and 342 through the orifice 54 in the object 5, thereby preventing the object 5 from being removed from the strip 3 unless the operator imparts elastic deformation.

In an embodiment that is not shown in the figures, provision may be made for said coupling system 4 to include two spaced-apart parallel slots arranged through the strip 3 in order to form a loop in which an object, such as a screw, can be inserted along an insertion direction perpendicular to the slot.

Advantageously, the shape of the tube 1 and the shape of the strip 3 are configured to limit or prevent the strip 3 from turning relative to the tube 1. Such a configuration enables the object 5 to be held in a given position suspended in air without any risk of the object being degraded by impacts against the wall of the tube.

FIGS. 5 to 9 show various steps enabling an object 5 to be extracted from a packaging device, such as that shown in FIG. 1.

Figure 5:
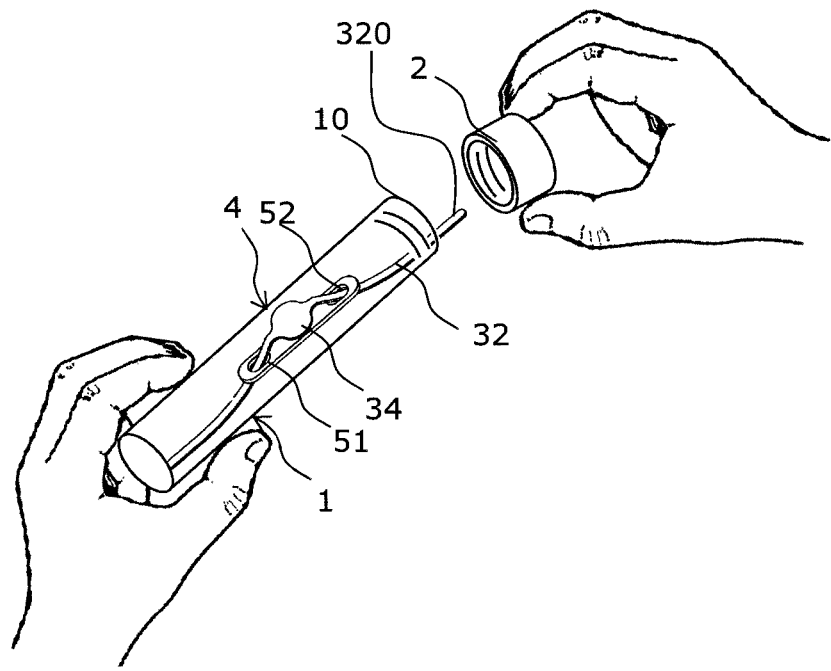
FIGS. 5 to 9 are views showing different steps performed by an operator in order to grip the strip used for coupling the implant, to grip the implant, and to decouple it from the strip.
Figure 6:
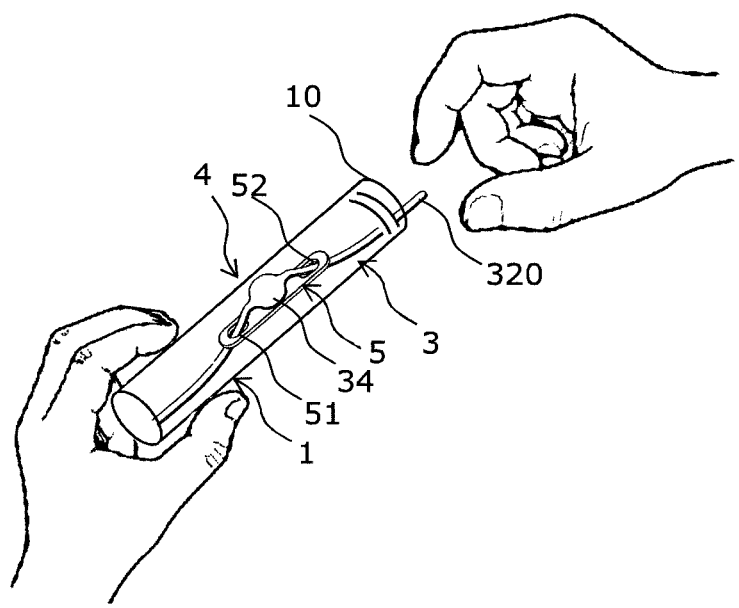
Figure 7:
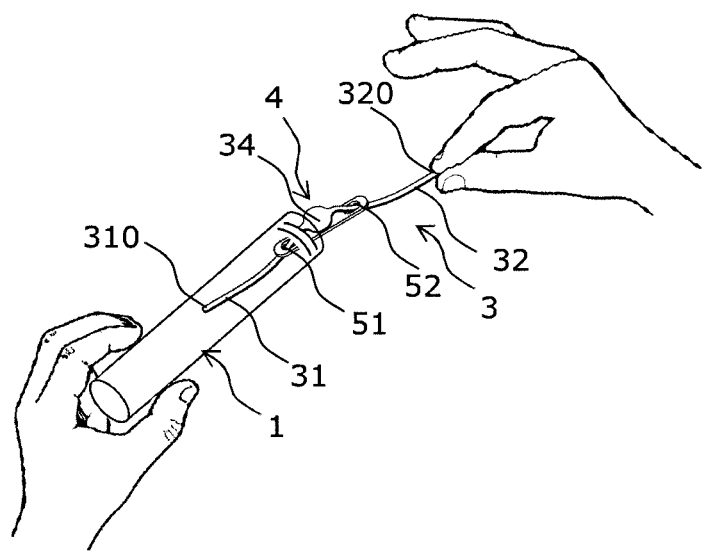
Figure 8:
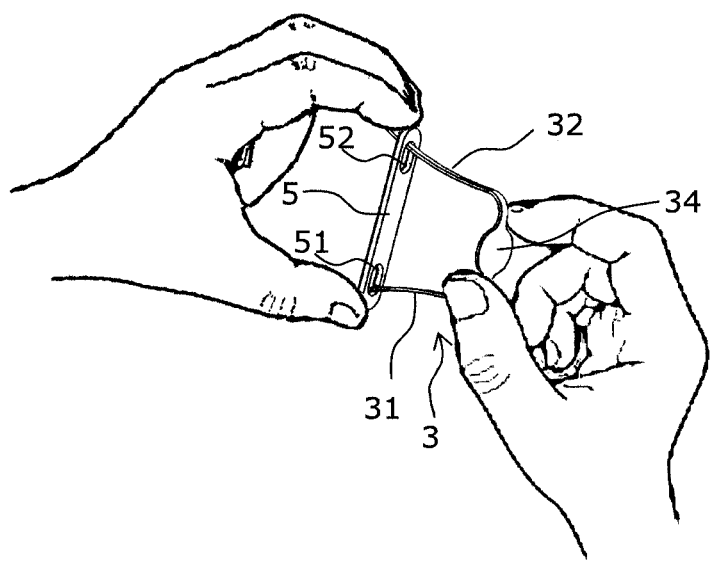
Figure 9:
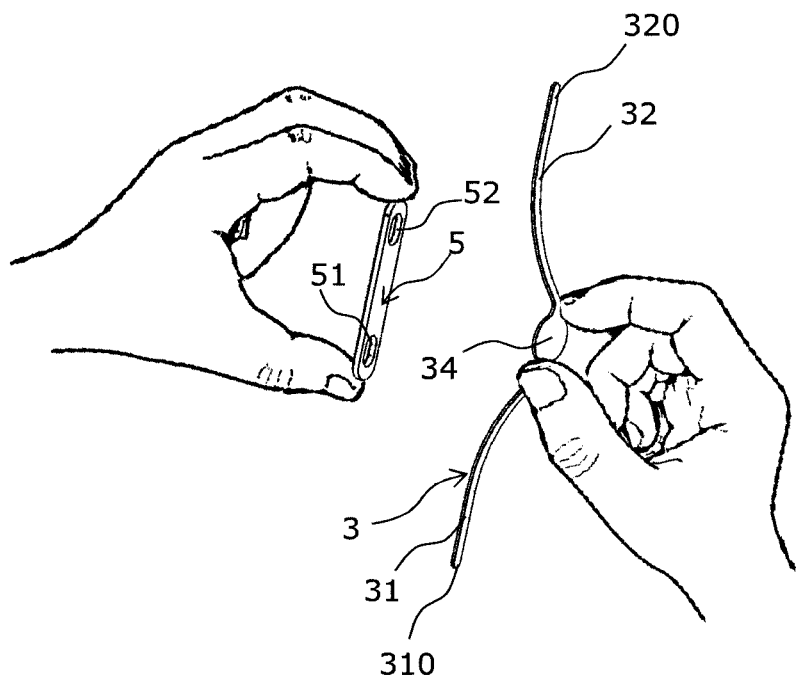

As shown in FIG. 5, the operator removes the stopper 2 in order to open the tube 1, and then grips the end 320 of the strip that projects out through the opening 10 of the tube 2 (FIG. 6) in one hand in order to extract it from the tube (FIG. 7) together with the object 5 that is attached thereto. The operator can then use the other hand to grip the object 5 while still coupled to the strip 3 and than decouple it by removing the strip (FIG. 8).

In the examples shown in FIGS. 1 and 2, decoupling is performed by pulling on the enlarged portion 34 in order to move the enlarged portion of the strip away from the object so as to cause the ends 310 and 320 of the strip to be extracted from the orifices 51 and 52 in the object 5.

In the embodiment shown in FIG. 3, decoupling is performed by pressing against the element 340 in order to bring its two portions towards the slot of said element and cause it to pass through the orifice in the object by pulling on the enlarged portion 34B in order to move the enlarged portion of the strip away from the object and cause the ends 310 and 320 of the strip to be extracted from the orifices 51 and 52 in the object 5.

In similar manner, in the embodiment shown in FIG. 4, decoupling is performed by moving the two lugs 341 and 342 towards each other so as to cause them to pass through the orifice in the object by pulling on the enlarged portion 340 so as to move the enlarged portion 340 of the strip 3 away from the object and cause the ends 310 and 320 of the strip to be extracted through the orifice 54 in the object 5.

Figure 10:
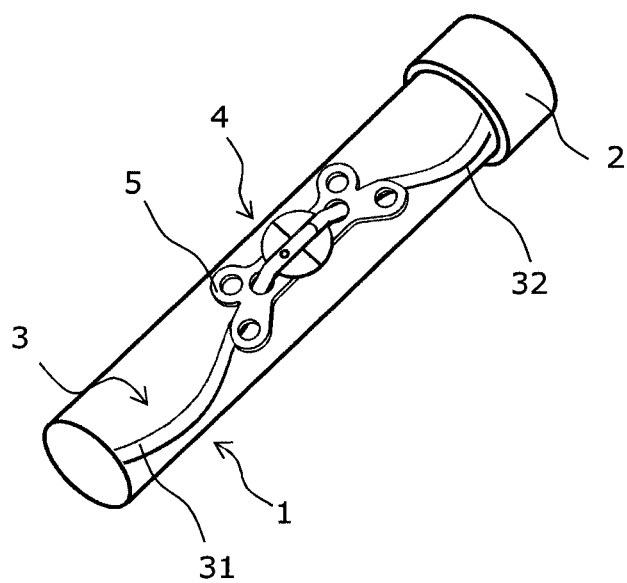
FIG. 10 is a view of the tube closed by a stopper, said tube containing an implant coupled to a flexible strip, in accordance with a fourth embodiment of the invention.

FIG. 10 shows another embodiment of the invention in which the strip is made in two portions. The two portions are suitable for assembling and disassembling relative to each other, preferably by snap-fastening. The connection zone between the two portions is preferably situated halfway along the strip. By making the strip in two portions, it is possible, when the through orifices in the object are abrasive, to withdraw the object from the strip by disassembling the strip and thus avoiding the need to pull the entire length of the strip with friction against the through orifices, which might generate debris. By disassembling the strip into its two portions, the amount the strip bears against the through orifices is reduced.

Figure 11:
FIG. 11 is a section view of a flexible strip in accordance with an embodiment of the invention.
Figure 12:
FIG. 12 is a section view of a flexible strip in accordance with another embodiment of the invention.

As shown in FIG. 11, the strip may be elliptical in section, e.g. as obtained by injecting a thermoplastic polymer such as styrene-ethylene-butylene-styrene (SEBS): polystyrene-b-poly(ethylene-butylene)-b-polystyrene. The strip may also be trapezoidal in section (FIG. 12), e.g. being obtained by being cut out from a sheet of material such as glycol-modified polyethylene terephthalate (PET-G). Sections of other shapes can be envisaged.

Figure 13:
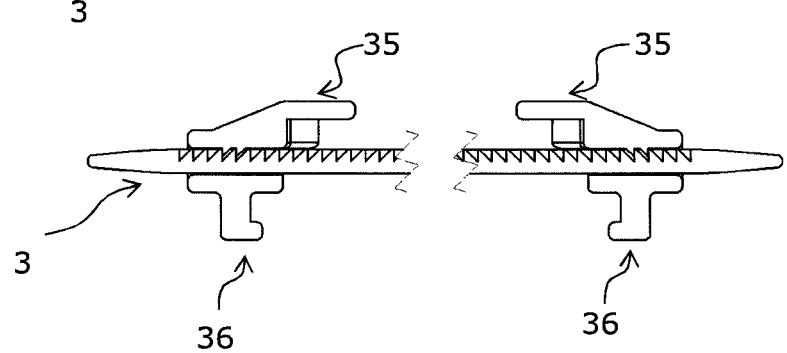
FIG. 13 is a perspective view of a flexible strip in accordance with another embodiment of the invention in which the strip is in the form of a rack provided with sliders.
Figure 14:
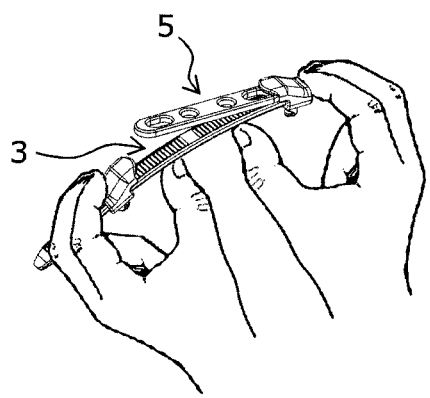
FIG. 14 is a perspective view of a flexible strip in accordance with the embodiment of FIG. 13, shown in a flexed state in order to recover the object that was previously held by the sliders.

In a particular embodiment shown in FIGS. 13 and 14, the strip 3 is in the form of a rack having sliders 35. Advantageously, the rack is also provided with coupling elements 36 for enabling the rack to be coupled with the object 5 when the object presents orifices in which said coupling element can be engaged. Advantageously, said coupling elements 36 are in the form of studs situated beside one of the faces of the rack, opposite from the active portions of the sliders 35. Said coupling elements 36 are suitable for engaging through orifices in the object.

The sliders 35 are movable towards each other along detents on the rack in order to clamp the object 5. The detents are configured to co-operate with the sliders so as to allow the sliders to slide relative to each other only on going towards each other.

In the example shown in the figures, the studs 36 are carried by the sliders 35. Thus, each slider 35 has on one side an active portion in the form of a cradle for gripping the object from the outside, and on the other side pegs or studs 36 for holding the object by means of its fastening orifices or its concave zones.

Such a strip provided with sliders as shown in FIGS. 13 and 14 makes it possible to grip the object from the outside of said object. Thus, once the stopper of the tube has been opened and the strip 3 has been extracted from the tube, the object 5 held by the active portions of the sliders or by the studs can easily be recovered (without friction) by causing the rack to flex (as shown in FIG. 14).

The invention is not limited to the embodiments shown in the drawings. Consequently, it should be understood that when characteristics mentioned in the accompanying claims are followed by reference signs, those signs are given solely for the purposes of improving the intelligibility of the claims and are not in any way limiting on the scope of the claims.

Furthermore, the term "comprising" does not exclude other elements or steps. In particular, characteristics or steps that are described with reference of any of the above-described the embodiments may equally well be used in combination with other characteristics or steps of other embodiments that are described above.

The invention claimed is:

1. A packaging device for packaging an object, the device comprising:
   a tube that is open at one end; and
   a stopper enabling an opening of the tube to be closed;
   the packaging device being characterized in that it comprises a flexible elongate element referred to as a "strip";
   said strip being of length greater than the length of the tube;
   said strip having a coupling system enabling an object, such as a medical implant, to be coupled to said strip;
   together with the tube, the strip being configured to occupy:
      a first position in which the strip is held compressed inside the tube by the stopper, said strip presenting a first end in bearing contact with the end wall of the tube opposite from the said opening; and
      a second position in which, after the stopper has been removed, the strip presents a second end, opposite from said first end, that projects out through the opening of the tube.

2. A device according to claim 1, wherein the tube is translucent or transparent.

3. A device according to claim 1, wherein the coupling system comprises an element suitable for snap-fastening with an orifice formed in the object.

4. A device according to claim 1, wherein said coupling system comprises an enlarged portion of the strip, preferably situated in the middle of the strip, that forms a base, two lugs being formed by being cut out in said base, said lugs being suitable for being stood up relative to said base, so as to be brought one against the other in order to be passed through an orifice formed in the object, said lugs being suitable for returning to a mutually spaced-apart position after passing through the orifice in the object, in which position the possibility of removing the object is limited.

5. A device according to claim 1, wherein the strip is in the form of a rack presenting a series of detents and the coupling system comprises two sliders that can be moved towards each other along the rack in order to clamp onto the object, the detents being configured to prevent said sliders from moving away from each other.

6. A device according to claim 1, wherein the tube and the strip are shaped in such a manner as to limit or prevent the strip from turning relative to the tube.

7. A device according to claim 1, wherein said device includes said object, said object being coupled to the strip and being contained in the tube.

8. A device according to claim 7, wherein a first orifice and a second orifice are formed in the object in order to pass one end portion of the strip through the first orifice and pass an opposite end portion of the strip through the second orifice, in such a manner that the coupling system of the strip extends on one side of the object and the end portions extend mainly on the other side.

9. A device according to claim 8, wherein the coupling system comprises a portion of the strip, referred to as a "stop portion", that is spaced apart from the ends of the strip, and that is of width greater than the width of the end portions of the strip and greater than the width of the first and second orifices formed in the object.

10. A method of extracting the object from the packaging device according to claim 7, said method comprising the following steps:
   removing the stopper in order to open the tube;
   the operator gripping in one hand the end portion of the strip that projects through the opening of the tube;
   gripping in another hand the object coupled to the strip; and
   decoupling the object from the strip.

* * * * *